United States Patent [19]

Nies

[11] Patent Number: 6,147,053
[45] Date of Patent: *Nov. 14, 2000

[54] COMBINATION CONTAINING GROWTH FACTORS AND POLYELECTROLYTES

[75] Inventor: Berthold Nies, Ober-Ramstadt, Germany

[73] Assignee: Merck Patent Gesellschaft MIT, Germany

[*] Notice: This patent is subject to a terminal disclaimer.

[21] Appl. No.: 09/198,533

[22] Filed: Nov. 24, 1998

Related U.S. Application Data

[63] Continuation of application No. 08/330,619, Oct. 28, 1994, Pat. No. 5,885,960, which is a continuation of application No. 07/950,566, Sep. 25, 1992, abandoned.

[30] Foreign Application Priority Data

Sep. 26, 1991 [DE] Germany ............................. 41 32 005

[51] Int. Cl.$^7$ ............................. A61K 38/00; A61K 31/74
[52] U.S. Cl. .................................. 514/12; 514/2; 514/925; 514/926; 514/927; 514/928; 514/866; 514/944; 424/78.08; 424/DIG. 13; 424/600
[58] Field of Search .................................. 514/2, 12, 925, 514/926, 927, 928, 866; 424/600, 78.08, DIG. 13, 484

[56] References Cited

U.S. PATENT DOCUMENTS

| 4,783,412 | 11/1988 | Bell ...................................... 435/240.1 |
| 4,956,455 | 9/1990 | Esch et al. .............................. 530/399 |
| 5,885,960 | 3/1999 | Nies . |

FOREIGN PATENT DOCUMENTS

| 200574 | 6/1986 | European Pat. Off. . |
| 312208 | 9/1988 | European Pat. Off. . |
| 01728 | 3/1987 | WIPO . |

OTHER PUBLICATIONS

"Molecular Biology of the Cell," (eds., Alberts et al.).

*Primary Examiner*—Thurman K. Page
*Assistant Examiner*—Todd Ware
*Attorney, Agent, or Firm*—Millen, White, Zelano & Branigan, P.C.

[57] ABSTRACT

The invention relates to active substance combinations which consist of at least one polypeptide with the biological action of fibroblast growth factors and of at least one cationic polyelectrolyte. These combinations permit improved dosage of the FGF activity.

14 Claims, No Drawings

COMBINATION CONTAINING GROWTH FACTORS AND POLYELECTROLYTES

This is a continuation of the application Ser. No. 08/330,619, filed Oct. 28, 1994, now U.S. Pat. No. 5,885,960, which in turn is a CONT of Ser. No. 07/950,566 filed Sep. 25. 1992, abandoned.

SUMMARY OF THE INVENTION

The invention relates to compositions which, besides at least one polypeptide with the biological activity of fibroblast growth factors (FGF), contain at least one cationic polyelectrolyte.

Fibroblast growth factors (FGF) which belong to the class of endogenous peptide growth factors, were originally detected as substances in the brain and pituitary and isolated therefrom and showed an activity promoting the growth of fibroblasts. FGFs are known to be effective angiogenic factors which are responsible, inter alia, for neovascularization in wound healing. More details on FGFs, including their modification products, on their isolation and preparation, their structure, their biological activities and their mechanisms, and on corresponding medical uses can be found in the specialist literature which is now wide-ranging. A comprehensive review is provided, for example, by A. Baird and P. Böhlen, Fibroblast Growth Factors in: Peptide Growth Factors and their Receptors I (editors: M. B. Sporn and A. B. Roberts) Springer Verlag Berlin, Heidelberg, New York 1990.

Growth factors regarded as suitable according to the invention are not only the "classical" FGFs such as acidic fibroblast growth factor (aFGF) and basic fibroblast growth factor (bFGF) but also all peptides which essentially display the biological activity of FGF.

FGFs in the narrower sense include natural FGFs especially of bovine and human origin, as well as FGFs prepared recombinantly. Particularly preferred are human aFGF and bFGF prepared recombinantly. Details on bovine and human and aGFG and bFGF as prepared recombinantly can be found in the following patent documents, for example: EP 0 228 449, EP 0 248 819, EP 0 259 953, EP 0 275 204. FGFs in the wider sense also include muteins which differ from aFGF and bFGF to a certain extent in the number and/or sequence of the amino acids without thereby being associated with a substantial alteration in the action. In addition, the generic term is to be understood to cover, for example, various forms of bFGF which differ in their length: they contain 146, 153, 154 or 157 amino-acid residues. Finally, FGFs in the wider sense also embrace related peptides, some of which have distinctly different amino-acid sequences but have the biological activity of FGF. The following patent documents may be mentioned by way of example with reference to the literature: EP 0 148 922, EP 0 226 181, EP 0 281 822, EP 0 288 307, EP 0 319 052, EP 0 326 907 and WO 89-12645. The said peptides are comprised by "peptides with FGF activity" for simplification.

FGFs within the meaning of the invention furthermore include derivatives of these peptides which are obtained with stabilizing and/or activity-increasing agents. These are, in particular, forms of aFGF and bFGF stabilized against acid, which contain as stabilizing agents, for example, glycosaminoglycans such as heparin, heparin fragments, heparin sulfate and dermatan sulfate or glucan sulfates such as dextran sulfate and cyclodextrin sulfate. FGF derivatives of this type are described, for example, in EP 251 806, EP 267 015, EP 312 208, EP 345 660, EP 406 856, EP 408 146, WO 89-12464, WO 90-01941 and WO 90-03797.

Preferred for the present invention are FGFs of human origin and the muteins thereof, especially bFGF. It is particularly preferred to use human bFGF prepared recombinantly, as described in EP 0 248 819.

It is common to the peptides with FGF activity that they bind specifically to the FGF receptors of the cell membrane and then display their biological action, for example in wound healing. The result of this binding is that, for example, bFGF cannot normally be detected in serum even after injection. For example, bFGF as a basic protein (IP=9.8) is bound to anionic macromolecules (for example, nucleic acids and acidic components of the extracellular matrix (ECM) such as heparin sulfate—see, inter alia, Moscatelli et al.: Interaction of basic fibroblast growth factor with extracellular matrix and receptors. Lecture at a conference on "The Fibroblast Growth Factor Family" arranged by The New York Academy of Sciences, 1991). This property is described in the literature and is utilized, inter alia, for the isolation of FGFs: purification of a- and bFGF by chromatography on supports which contain bound heparin.

The non-specific binding of the peptides with FGF activity reduces the amount of FGF able to reach the specific receptor on the cell. In the particular case of relatively old (chronic) wounds or burn wounds, or when large amounts of necrotic material are present, the non-specific binding will absorb a large and, at the same time, unknown portion of the FGF. This is why accurate dosage of the effective amount of peptides with FGF activity is impossible. Overdosage of the active substance is necessary. This means that the dosage is also unreliable because it is unknown how many non-specific binding sites are present in the particular wound.

Attempts to stabilize bFGF, to reduce its non-specific binding and to increase its affinity for the specific receptor have hitherto entailed combining bFGF with heparin or other sulfated glycans (for example, dextran sulfate) or sucralfate. However, at present, bFGF is normally tested without such additives. The only ancillary substances added are for stability and improved administration.

The disadvantage of the use of pure bFGF and, to varying extents, also the said combinations and derivatives comprises the necessity for overdosage of the active substance and the unreliability of dosage because it is unknown how many non-specific binding sites are present in the particular wound.

An object of the invention is therefore to provide a combination of active substances whose biological activity is unaffected by the non-specific binding of the peptides with FGF activity.

Upon further study of the specification and appended claims, further objects and advantages of this invention will become apparent to those skilled in the art.

It is true that EP 0 312 208 proposes employing gel formers together with growth factors, preferably epidermal growth factor (EGF), for improved dosage by means of diffusion control. However, this measure does not solve the fundamental problem of the dosage of growth factors, which results from the variable non-specific binding.

It has now been found that these dosage problems can be solved by additional administration of at least one cationic polyelectrolyte on administration of peptides with FGF activity. It is surprising in this connection that although the cationic polyelectrolytes block the non-specific binding sites, for example in the ECM, nevertheless the peptides with FGF activity are able to reach their specific receptors in the cell membrane, and thus the biological activity of FGF is retained. The composition of this invention excludes the compositions of EP 0 312 208 which incidently contain cationic polyelectrolytes, whose disclosure is hereby incorporated by reference.

The cationic polyelectrolyte typically is a polymer having a positive net charge in solution and which lacks specific growth activity.

It is possible to use, according to the invention, a number of known cationic polyelectrolytes. It is common to them that they irreversibly form complexes under physiological conditions with cell structures or binding sites which bind FGF non-specifically. Examples of suitable cationic polyelectrolytes are polyamines and -imines, as well as their quaternized derivatives. Also suitable are polyguanidines, as well as polypeptides which contain basic amino acids; for example, polylysine, polyornithine, polyarginine. It is also possible for polypeptides of these types to contain mixtures of a plurality of amino acids. The amino acids themselves can be employed either in racemic form or in pure D or L form in the peptides used according to the invention. Also suitable are polysaccharides with basic groups. It is particularly preferred to use chitosans and their derivatives, for example, N-carboxybutylchitosan or methylpyrrolidonechitosan, because these are biodegradable and the degradation products are identical to components of normal metabolism (glucosamine and N-acetylglucosamine). Cationic polyelectrolytes having molecule weights of 500 daltons or greater are preferred. It is also preferred that the cationic polyelectrolyte does not substantially increase the solution viscosity, e.g., the value is, 2 cps or less, preferably is 1 cps or less and preferably is not increased at all.

It is possible according to the invention to employ the cationic polyelectrolytes as free bases or else as salts with physiologically tolerated organic or inorganic acids. Examples of physiologically tolerated organic acids are glutamic acid, acidic acid and lactic acid. Hydrochloric acid is mentioned as example of a physiologically tolerated inorganic acid. Other physiologically tolerated acids are known to the pharmaceutical technologist.

These substances are administered in excess compared with the peptides with FGF activity and at the same time as the latter. It is likewise possible to administer the cationic polyelectrolytes first. This results in FGFs being able to diffuse unhindered to the specific receptor and bind thereto. However, it is also conceivable within the scope of the procedure according to the invention to administer the cationic polyelectrolytes subsequently in order to displace the FGFs from the non-specific binding sites. The advantage of this procedure is the possibility in each case of using a comparatively low dose of the peptides with FGF activity, which results in a corresponding increase in the therapeutic index. In addition, considerably more reliable use can be achieved, since the FGFs are able to reach the target site even in the case of highly necrotic wounds. Multiple administration is often indicated in such cases.

The invention therefore relates to combinations which contain at least one polypeptide with FGF activity and at least one cationic polyelectrolyte lacking specific growth activity.

The combinations according to the invention can in this connection preferably be in the form of aqueous solutions which, besides at least one polypeptide with FGF activity and at least one cationic polyelectrolyte, contain customary additives such as buffer substances or salts to regulate the osmotic pressure or else fillers. The concentration of the polypeptides with FGF action in these solutions is 0.1 ng/ml–500 μg/ml, preferably 0.5 ng/ml–300 μg/ml, and that of the cationic polyelectrolytes is 1 μg/ml–300 mg/ml, preferably 0.1 mg/ml–200 mg/ml. These solutions can be further processed in a known manner by adding gel formers to give hydrogels. The solutions, where appropriate with added fillers, or hydrogels can be dried or lyophilized to give web materials, to give films, to give powders, to give granules or to give threads. Threads obtained in this way can be further processed to give woven fabrics or nets. It is also possible to absorb these solutions in wound gauze or in wound closure film and to dry the latter. The dried presentations can also be used, reconstituted with liquid, as aqueous solution or as gel or hydrogel for wound dressing. Finally, the combinations according to the invention can also be in the form of a reagent assemblage (kit) in which the components (peptide with FGF activity and cationic polyelectrolyte) are present separately but in balanced amounts.

In the case of fresh, clean wounds, a small excess of cationic polyelectrolyte, i.e., at least about five times the amount of peptides with FGF activity, is sufficient for the masking. However, this excess must be considerably increased appropriate for the state of the wound in order to block the non-specific binding sites. For this reason it is possible according to the invention for the amount of cationic polyelectrolyte to be up to ten thousand times the amount of the peptides with FGF activity. The ratio between the amounts by weight of cationic polyelectrolyte lacking specific growth activity and peptide with FGF activity is preferably 100–2,000.

The invention furthermore -relates to the use of an addition of at least one cationic polyelectrolyte lacking specific growth activity to a preparation which contains at least one peptide with FGF activity in order to block non-specific binding sites for the peptide with FGF activity.

The invention relates to processes for the preparation of combinations which contain at least one peptide with FGF activity and, in addition, at least one cationic polyelectrolyte, wherein the components are preferably present as aqueous solution, and furthermore can contain customary additives such as buffer substances or salts to regulate the osmotic pressure or else fillers. These solutions can also be sterilized. It is additionally possible to process these solutions further to give semisolid or solid presentations, for example hydrogels, webs, threads, woven fabrics, granules, powders, impregnated materials.

The invention relates to processes for the preparation of pharmaceutical compositions, in which a combination which contains at least one peptide with FGF activity and, in addition, at least one cationic polyelectrolyte is converted with at least one solid, liquid or semiliquid vehicle or ancillary substance into a suitable dosage form.

The invention relates to pharmaceutical compositions which contain combinations composed of at least one peptide with FGF activity and, in addition, at least one cationic polyelectrolyte.

The invention relates to the use of combinations which contain at least one peptide with FGF activity and, in addition, at least one cationic polyelectrolyte for controlling diseases.

The invention relates to the use of a combination which contains at least one peptide with FGF activity and, in addition, at least one cationic polyelectrolyte for the preparation of a pharmaceutical.

The combinations according to the invention can advantageously be employed for the therapy of wounds for which FGF therapy is indicated, especially when free granulation processes are involved in the healing of these wounds or defects. Important areas of application of the combinations according to the invention are ulcers of the skin (for example pressure sores, diabetic gangrene, arterial and venous congestion), in addition wounds from burns, mucosal ulcers and lesions, skin donation sites, skin and soft-tissue transplantation sites (preparation of the floor of the wound) and surgical wounds (especially where healing functions are impaired). For all these areas of application the administration of combinations of peptides with FGF activity and suitable polycations is particularly important when the patients' wound-healing capacity is impaired (for example because of age, basic diseases or therapeutic measures).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 41 32 005.0 filed Sep. 26, 1991, are hereby incorporated by reference.

EXAMPLES

The preparation and use of the combinations according to the invention is described by way of example hereinafter, but this description is not to be regarded as a restriction of the subject matter of the invention. The advantages compared with the FGF-containing preparations known to date from the state of the art become clear from the reported examples of use.

Example 1

Example 1a

Chitosan Solution 100 mg of chitosan glutamate (manufactured by Protan Co., Norway) are dissolved in 10 ml of Ringer's solution.

Example 1b bFGF Solution

100 $\mu$g of human bFGF prepared recombinantly are dissolved in 10 ml of 20 mM citrate buffer pH 5.0.

Example 1c

Combined Chitosan-bFGF Solution 10 ml each of the solutions from Examples 1a and 1b are mixed. The final concentration of bFGF is 5 $\mu$g/ml.

Example 2

Example 2a

Chitosan Solution 100 mg of methylpyrrolidone-chitosan (produced according to Muzzarelli, WO 91/02 168) are dissolved in 10 ml of aqueous sodium chloride solution (9 g/l).

Example 2b bFGF Solution

50 $\mu$g of human bFGF prepared recombinantly are dissolved in 10 ml of 20 mM citrate buffer pH 5.0.

Example 2c

Combined Chitosan-bFGF Solution 10 ml each of the solutions from Examples 2a and 2b are mixed. The final concentration of bFGF is 2.5 $\mu$g/ml.

EXAMPLE 3

After preparation of the solution from Example 1c it is lyophilized in a layer thickness of 2–5 mm. The result is a web which contains active substance and is suitable for covering wounds.

EXAMPLE 4

Commercially available wound dressing gauze is impregnated with a solution from Example 2c (2 ml/5 cm$^2$) and then dried. The result is a gauze which contains active substance and is suitable for covering wounds.

Use Example A

The viscous solution from Example 1c is uniformly applied at about 1 ml/5 cm$^2$ area of wound to the wound to be treated.

Use Example B

The wound is first pretreated with a solution from Example 1a (chitosan) about 1 ml/5 cm$^2$ area of wound). After a pretreatment time of about 30 minutes, the excess solution and wound discharge are removed with a swab. The wound is subsequently treated further with a solution from Example 1b (bFGF) (about 1 ml/5 cm$^2$ area of wound).

Use Example C

The wound is first pretreated with a solution from Example 1a (chitosan) (about 1 ml/5 cm$^2$ area of wound). After a pretreatment time of about 30 minutes, the excess solution and wound discharge are removed with a swab. The wound is subsequently treated further with a solution from Example 1c (combination of chitosan and bFGF) (about 1 ml/5 cm$^2$ area of wound).

The latter method has the advantage that the application of the combination of bFGF and chitosan results in bFGF-binding substances which have been newly discharged into the area of the wound are absorbed.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition, consisting essentially of 0.1 ng/ml–500 $\mu$g/ml of an FGF peptide and a cationic polyelectrolyte, wherein, when the composition is in solution, the cationic polyelectrolyte is bioavailable in an amount effective to decrease non-specific binding of the FGF peptide.

2. A composition according to claim 1, wherein the amount of cationic polyelectrolyte is 1 µg/ml–300 mg/ml.

3. A composition according to claim 2, wherein the amount of cationic polyelectrolyte is 0.1 mg/ml–200 mg/ml.

4. A pharmaceutical composition of claim 1, wherein the cationic polyelectrolyte is not chitosan.

5. The pharmaceutical composition of claim 1, wherein the cationic polyelectrolyte is a chitosan derivative.

6. A pharmaceutical composition of claim 1 further comprising a pharmaceutically acceptable carrier.

7. A pharmaceutical composition, consisting essentially of 0.1 ng/ml–500 µg/ml of FGF peptide and a cationic polyelectrolyte wherein the cationic polyelectrolyte is bioavailable in an amount effective to decrease non-specific binding of the FGF peptide, and wherein, when the composition is in solution, the cationic polyelectrolyte does not increase the viscosity of the solution.

8. A pharmaceutical composition of claim 7 further comprising a pharmaceutically acceptable carrier.

9. A pharmaceutical composition of claim 1, wherein said cationic polyelectrolyte lacks specific growth activity.

10. A pharmaceutical composition of claim 7, wherein said cationic polyelectrolyte lacks specific growth activity.

11. A pharmaceutical composition of claim 1, wherein the weight ratio of the cationic polyelectrolyte to the FGF peptide is 5:1 to 10,000:1.

12. A pharmaceutical composition of claim 1, wherein the weight ratio of the cationic polyelectrolyte to the FGF peptide is 100:1 to 2,000:1.

13. A web material, comprising a dried pharmaceutical composition, consisting essentially of 0.1 ng/ml–500 µg/ml of an FGF peptide and a cationic polyelectrolyte, wherein, when the composition is in solution, the cationic polyelectrolyte is bioavailable in an amount effective to decrease non-specific binding of the FGF peptide.

14. A wound dressing gauze, consisting essentially of a dried pharmaceutical composition, comprising 0.1 ng/ml–500 µg/ml of an FGF peptide and a cationic polyelectrolyte, wherein, when the composition is in solution, the cationic polyelectrolyte is bioavailable in an amount effective to decrease non-specific binding of the FGF peptide.

* * * * *